US008412338B2

(12) United States Patent
Faltys

(10) Patent No.: US 8,412,338 B2
(45) Date of Patent: Apr. 2, 2013

(54) DEVICES AND METHODS FOR OPTIMIZING ELECTRODE PLACEMENT FOR ANTI-INFLAMATORY STIMULATION

(75) Inventor: Michael A. Faltys, Valencia, CA (US)

(73) Assignee: SetPoint Medical Corporation, Valencia, CA (US)

( * ) Notice: Subject to any disclaimer, the term of this patent is extended or adjusted under 35 U.S.C. 154(b) by 457 days.

(21) Appl. No.: 12/620,413

(22) Filed: Nov. 17, 2009

(65) Prior Publication Data

US 2010/0125304 A1 May 20, 2010

Related U.S. Application Data

(60) Provisional application No. 61/115,806, filed on Nov. 18, 2008.

(51) Int. Cl.
A61N 1/00 (2006.01)

(52) U.S. Cl. ........................................................ 607/50

(58) Field of Classification Search .................... 607/50
See application file for complete search history.

(56) References Cited

U.S. PATENT DOCUMENTS

| | | |
|---|---|---|
| 2,164,121 A | 6/1939 | Pescador |
| 3,363,623 A | 1/1968 | Atwell |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,049,659 A | 9/1991 | Cantor et al. |
| 5,073,560 A | 12/1991 | Wu et al. |

(Continued)

FOREIGN PATENT DOCUMENTS

| | | |
|---|---|---|
| DE | 2628045 A1 | 1/1977 |
| DE | 3736664 A | 5/1989 |

(Continued)

OTHER PUBLICATIONS

Faltys et al.; U.S. Appl. No. 12/917,197 entitled "Modulation of the cholinergic anti-inflammatory pathway to treat pain or addiction," filed Nov. 1, 2010.

(Continued)

Primary Examiner — Eric D. Bertram
(74) Attorney, Agent, or Firm — Shay Glenn LLP

(57) ABSTRACT

Described herein are methods, devices and system for selecting an optimum position of a stimulation electrode, and particularly methods, devices and systems for optimizing the position of a stimulation electrode for stimulating the inflammatory reflex and thereby inhibiting inflammation. The methods, devices and systems described herein may generally include the analysis of one or more artifact modalities arising after the application of a stimulation pulse. One or more of these artifact modalities (e.g., EMG, ECG, etc.) may be detected and used to generate a comparable indicator of the fitness of the position of the electrode relative to a target, such as a portion of the inflammatory reflex like the vagus nerve.

18 Claims, 6 Drawing Sheets

- Directionality: Only exhibited using monophasic stimulus when spacing is 4mm (15 vs >20 mA)
- FE Spacing (Biphasic): No difference between 1, 2, 4mm

U.S. PATENT DOCUMENTS

| | | | |
|---|---|---|---|
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thomspon et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 * | 8/2002 | Battmer et al. ............... 600/554 |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |

| Patent No. | Date | Name |
|---|---|---|
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,195,287 B2 | 6/2012 | Dacey, Jr. et al. |
| 8,214,056 B2 | 7/2012 | Hoffer et al. |
| 2001/0002441 A1 | 5/2001 | Boveja |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0125044 A1 | 6/2005 | Tracey |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0251220 A1 | 11/2005 | Barrett et al. |

| | | |
|---|---|---|
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0282906 A1 | 12/2005 | Tracey et al. |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0142802 A1 | 6/2006 | Armstrong |
| 2006/0142822 A1 | 6/2006 | Tulgar |
| 2006/0149337 A1 | 7/2006 | John |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0118177 A1 | 5/2007 | Libbus et al. |
| 2007/0118178 A1 | 5/2007 | Fukui |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0239243 A1 | 10/2007 | Moffitt et al. |
| 2007/0250145 A1 | 10/2007 | Kraus et al. |
| 2007/0255320 A1 | 11/2007 | Inman et al. |
| 2007/0255333 A1 | 11/2007 | Giftakis |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183246 A1 | 7/2008 | Patel et al. |
| 2008/0234790 A1 | 9/2008 | Bayer et al. |
| 2008/0249439 A1* | 10/2008 | Tracey et al. .................. 601/46 |
| 2008/0281365 A1 | 11/2008 | Tweden et al. |
| 2009/0012590 A1 | 1/2009 | Inman et al. |
| 2009/0048194 A1 | 2/2009 | Aerssens et al. |
| 2009/0062874 A1 | 3/2009 | Tracey et al. |
| 2009/0105782 A1 | 4/2009 | Mickle et al. |
| 2009/0123521 A1 | 5/2009 | Weber et al. |
| 2009/0125079 A1 | 5/2009 | Armstrong et al. |
| 2009/0143831 A1* | 6/2009 | Huston et al. .................. 607/2 |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0247934 A1 | 10/2009 | Tracey et al. |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2010/0003656 A1 | 1/2010 | Kilgard et al. |
| 2010/0010603 A1 | 1/2010 | Ben-David et al. |
| 2010/0042186 A1 | 2/2010 | Ben-David et al. |
| 2010/0063563 A1 | 3/2010 | Craig |
| 2010/0191304 A1 | 7/2010 | Scott |
| 2010/0215632 A1 | 8/2010 | Boss et al. |
| 2010/0241183 A1 | 9/2010 | Dilorenzo |
| 2010/0249859 A1 | 9/2010 | Dilorenzo |
| 2010/0280569 A1 | 11/2010 | Bobillier et al. |
| 2011/0004266 A1 | 1/2011 | Sharma |
| 2011/0066208 A1 | 3/2011 | Pasricha et al. |
| 2011/0092882 A1 | 4/2011 | Firlik et al. |
| 2012/0065706 A1 | 3/2012 | Vallapureddy et al. |

FOREIGN PATENT DOCUMENTS

| | | |
|---|---|---|
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2073896 B1 | 10/2011 |
| GB | 04133 | 2/1910 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO 00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO04/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO 2007/133718 A2 | 11/2007 |

OTHER PUBLICATIONS

Faltys et al.; U.S. Appl. No. 12/978,250 entitled "Neural stimulation devices and systems for treatment of chronic inflammation," filed Dec. 23, 2010.

Ben-Noun et al.; Neck circumference as a simple screening measure for identifying overweight and obese patients; Obesity Research; vol. 9; No. 8; pp. 470-477; Aug. 8, 2001.

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.

Bushby et al; Centiles for adult head circumference; Archives of Disease in Childhood; vol. 67; pp. 1286-1287; 1992.

Fields; New culprits in chronic pain; Scientific American; pp. 50-57; Nov. 2009.

Hansson, E.; Could chronic pain and spread of pain sensation be induced and maintained by glial activation?. Acta Physiologica, vol. 187: pp. 321R327, 2006.

Hutchinson et al.; Proinflammatory cytokines oppose opioid induced acute and chronic analgesia; Brain Behav Immun.; vol. 22; No. 8; pp. 1178-1189; Nov. 2008.

Miguel-Hidalgo, J.J.; The role of glial cells in drug abuse; Current Drug Abuse Reviews; vol. 2; No. 1; pp. 76-82; 2009.

Milligan et al.; Pathological and protective roles of glia in chronic pain; Nat Rev Neurosci.; vol. 10; No. 1; pp. 23-26; Jan. 2009.

Pulvirenti et al; Drug dependence as a disorder of neural plasticity:focus on dopamine and glutamate; Rev Neurosci.; vol. 12; No. 2; pp. 141-158; 2001.

Suter et al.; Do glial cells control pain?; Neuron Glia Biol.; vol. 3; No. 3; pp. 255-268; Aug. 2007.

Vijayaraghavan, S.; Glial-neuronal interactions-implications for plasticity anddrug addictionl AAPS J.; vol. 11; No. 1; pp. 123-132; 2009.

Abraham, Coagulation abnormalities in acute lung injury and sepsis, Am. J. Respir. Cell Mol. Biol., vol. 22, pp. 401-404, 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Antonica, A., et al., Vagal control of lymphocyte release from rat thymus, J. Auton. Nerv. Syst., vol. 48, pp. 187-197, 1994.

Asakura et al., Non-surgical therapy for ulcerative colitis, Nippon Geka Gakkai Zasshi, vol. 98, No. 4, pp. 431-437, Apr. 1997 (abstract only).

Benthem et al.; Parasympathetic inhibition of sympathetic neural activity to the pancreas; Am.J.Physiol Endocrinol.Metab; 280; pp. E378-E381; 2001.

Bernik et al., Vagus nerve stimulation attenuates cardiac TNF production in endotoxic shock, (supplemental to SHOCK, vol. 15, 2001, Injury, inflammation and sepsis: laboratory and clinical approaches, SHOCK, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression IN shock, New York Surgical Society, New York, NY, Apr. 11, 2001.

Bernik, et al., Pharmacological stimulation of the cholinergic anti-inflammatory pathway, The Journal of Experimental Medicine, vol. 195, No. 6, pp. 781-788, Mar. 18, 2002.

Besedovsky, H., et al., Immunoregulatory feedback between interleukin-1 and glucocorticoid hormones, Science, vol. 233, pp. 652-654, 1986.

Bhattacharya, S.K. et al., Central muscarinic receptor subtypes and carrageenin-induced paw oedema in rats, Res. Esp. Med. vol. 191, pp. 65-76, 1991.

Bianchi et al., Suppression of proinflammatory cytokines in monocytes by a tetravalent guanylhydrazone, Journal of Experimental Medicine, vol. 183, pp. 927-936, Mar. 1996.

Blackwell, T. S. et al., Sepsis and cytokines: current status, Br. J. Anaesth., vol. 77, pp. 110-117, 1996.

Blum, A. et al., Role of cytokines in heart failure, Am. Heart J., vol. 135, pp. 181-186, 1998.

Boldyreff, Gastric and intestinal mucus, its properties and physiological importance, Acta Medica Scandinavica (journal), vol. 89, pp. 1-14, 1936.

Borovikova et al., Acetylcholine inhibition of immune response to bacterial endotoxin in human macrophages, Abstracts, Society for Neuroscience, 29th Annual Meeting, Miami Beach, FL, Oct. 23-28, 1999, Abstract No. 624.6.

Borovikova et al., Efferent vagus nerve activity attenuates cytokine-mediated inflammation, Society for Neuroscience Abstracts, vol. 26, No. 102, 2000 (abstract only).

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.

Borovikova et al., Role of the efferent vagus nerve signal in the regulation of the innate immune response to LPS, (supplemental to SHOCK, vol. 13, 2000, Molecular, cellular, and systemic pathobiological aspects and therapeutic approaches, abstract, 5th World Congress on Trauma, Shock inflammation and sepsis-pathophysiology, immune consequences and therapy, Feb. 29-Mar. 4, 2000, Munich, DE), Abstract No. 166.

Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).

Borovikova et al., Vagotomy blocks the protective effects of I.C.V. CNI-1493 against LPS-induced shock, (Supplemental to SHOCK, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.

Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.

Borovikova, L. V., et al., Vagus nerve stimulation attenuates the systemic inflammatory response to endotoxin, Nature, vol. 405, No. 6785: pp. 458-462, May 25, 2000.

Bulloch et al.; Characterization of choline O-acetyltransferase (ChAT) in the BALB/C mouse spleen; Int.J.Neurosci.; 76; pp. 141-149; 1994.

Bumgardner, G. L. et al., Transplantation and cytokines, Seminars in Liver Disease, vol. 19, No. 2, pp. 189-204, 1999.

Burke et al., Bent pseudoknots and novel RNA inhibitors of type 1 human immunodeficiency virus (HIV-1) reverse transcriptase, J. Mol. Biol., vol. 264; pp. 650-666, 1996.

Cano et al.; Characterization of the central nervous system innervation of the rat spleen using viral transneuronal tracing; J.Comp Neurol.; 439; pp. 1-18; 2001.

Carteron, N. L., Cytokines in rheumatoid arthritis: trials and tribulations, Mol. Med. Today, vol. 6, pp. 315-323, 2000.

Corcoran, et al., The effects of vagus nerve stimulation on pro- and anti-inflammatory cytokines in humans: a preliminary report, NeuroImmunoModulation, vol. 12, pp. 307-309, 2005.

Das, Critical advances in spticemia and septic shock, Critical Care, vol. 4, pp. 290-296, Sep. 7, 2000.

Del Signore et al; Nicotinic acetylcholine receptor subtypes in the rat sympathetic ganglion: pharmacological characterization, subcellular distribution and effect of pre- and postganglionic nerve crush; J.Neuropathoi.Exp.Neurol.; 63(2); pp. 138-150; Feb. 2004.

Dibbs, Z., et al., Cytokines in heart failure: pathogenetic mechanisms and potential treatment, Proc. Assoc. Am. Physicians, vol. 111, No. 5, pp. 423-428, 1999.

Dinarello, C. A., The interleukin-1 family: 10 years of discovery, FASEB J., vol. 8, No. 15, pp. 1314-1325, 1994.

Doshi et al., Evolving role of tissue factor and its pathway inhibitor, Crit. Care Med., vol. 30, suppl. 5, pp. S241-S250, 2002.

Ellington et al., In vitro selection of RNA molecules that bind specific ligands, Nature, vol. 346, pp. 818-822, Aug. 30, 1990.

Esmon, The protein C pathway, Crit. Care Med., vol. 28, suppl. 9, pp. S44-S48, 2000.

Fleshner, M., et al., Thermogenic and corticosterone responses to intravenous cytokines (IL-1? and TNF-?) are attenuated by subdiaphragmatic vagotomy, J. Neuroimmunol., vol. 86, pp. 134-141, 1998.

Fox, D. A., Cytokine blockade as a new strategy to treat rheumatoid arthritis, Arch. Intern. Med., vol. 160, pp. 437-444, Feb 28, 2000.

Fox, et al., Use of muscarinic agonists in the treatment of Sjorgren' syndrome, Clin. Immunol., vol. 101, No. 3; pp. 249-263, 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, 1995.

Ghelardini et al., S-(–)-ET 126: A potent and selective M1 antagonist in vitro and in vivo, Life Sciences, vol. 58, No. 12, pp. 991-1000, 1996.

Ghia, et al., the vagus nerve: a tonic inhibitory influence associated with inflammatory bowel disease in a murine model, Gastroenterology, vol. 131, pp. 1122-1130, 2006.

Giebelen, et al., Stimulation of ?7 cholinergic receptors inhibits lipopolysaccharide-induced neutrophil recruitment by a tumor necrosis factor ?-independent mechanism, SHOCK, vol. 27, No. 4, pp. 443-447, 2007.

Goyal et al., Nature of the vagal inhibitory innervation to the lower esophageal sphincter, Journal of Clinical Investigation, vol. 55, pp. 1119-1126, May 1975.

Gracie, J. A., et al., A proinflammatory role for IL-18 in rheumatoid arthritis, J. Clin. Invest., vol. 104, No. 10, pp. 1393-1401, 1999.

Granert et al., Suppression of macrophage activation with CNI-1493 increases survival in infant rats with systemic haemophilus influenzae infection, Infection and Immunity, vol. 68, No. 9, pp. 5329-5334, Sep. 2000.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Guslandi, M., Nicotine treatment for ulcerative colitis, Br. J. Clin. Pharmacol., vol. 48, pp. 481-484, 1999.

Harrison's Principles of Internal Medicine, vol. 13, pp. 511-515 and 1433-1435, 1994.

Hirano, T., Cytokine suppresive agent improves survival rate in rats with acute pancreatitis of closed duodenal loop, J. Surg. Res., vol. 81, No. 2, pp. 224-229, 1999.

Hirao et al., the limits of specificity: an experimental analysis with RNA aptamers to MS2 coat protein variants, Mol. Divers., vol. 4, pp. 75-89, 1999.

Holladay et al., Neuronal nicotinic acetylcholine receptors as targets for drug discovery, Journal of Medicinal Chemistry, 40, pp. 4169-4194, 1997.

Hommes, D. W. et al., Anti- and Pro-inflammatory cytokines in the pathogenesis of tissue damage in Crohn's disease, Current Opinion in Clinical Nutrition and Metabolic Care, vol. 3., pp. 191-195, 2000.

Hsu, et al., Analysis of efficiency of magnetic stimulation, IEEE Trans. Biomed. Eng., vol. 50(11), pp. 1276-1285, Nov. 2003.

Hsu, H. Y., et al., Cytokine release of peripheral blood monoclear cells in children with chronic hepatitis B virus infection, J. Pediatr. Gastroenterol., vol. 29, No. 5, pp. 540-545, 1999.

Hu, et al., The effect of norepinephrine on endotoxin-mediated macrophage activation, J. Neuroimmunol., vol. 31, pp. 35-42, 1991.

Huston et al.; Splenectomy inactivates the cholinergic antiinflammatory pathway during lethal endotoxemia and polymicrobial sepsis; J. Exp. Med. 2006; vol. 203; pp. 1623-1628; 2006.

Ilton et al., "Differential expression of neutrophil adhesion molecules during coronary artery surgery with cardiopulmonary bypass" Joumal of Thoracic and Cardiovascular Surgery, Mosby-Year Book, inc., St. Louis, Mo, US, pp. 930-937, Nov. 1, 1999.

Jaeger et al., The structure of HIV-1 reverse transcriptase complexed with an RNA pseudoknot inhibitor, The EMBO Journal, 17(15), pp. 4535-4542, 1998.

Jander, S. et al., Interleukin-18 is induced in acute inflammatory demyelinating polymeuropathy, J. Neuroimmunol., vol. 114, pp. 253-258, 2001.

Joshi et al., Potent inhibition of human immunodeficiency virus type 1 repletion by template analog reverse transcriptase , J. Virol., 76(13), pp. 6545-6557, Jul. 2002.

Kanai, T. et al., Interleukin-18 and Crohn's disease, Digestion, vol. 63, suppl. 1, pp. 37-42, 2001.

Katagiri, M., et al., Increased cytokine production by gastric mucosa in patients with helicobacter pylori infection, J. Clin, Gastroenterol., vol. 25, Suppl. 1, pp. S211-S214, 1997.

Kawashima, et al., Extraneuronal cholinergic system in lymphocytes, Pharmacology & Therapeutics, vol. 86, pp. 29-48, 2000.

Kees et al; Via beta-adrenoceptors, stimulation of extrasplenic sympathetic nerve fibers inhibits lipopolysaccharide-induced TNF secretion in perfused rat spleen; J.Neuroimmunol.; 145; pp. 77-85; 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Kimball, et al., Levamisole causes differential cytokine expression by elicited mouse peritoneal macrophases, Journal of Leukocyte Biology, vo. 52, No. 3, pp. 349-356, 1992 (abstract only).

Kimmings, A. N., et al., Systemic inflammatory response in acute cholangitis and after subsequent treatment, Eur. J. Surg., vol. 166, pp. 700-705, 2000.

Kirchner et al.; Left vagus nerve stimulation suppresses experimentally induced pain; Neurology; vol. 55; pp. 1167-1171; 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Kumins, N. H., et al., Partial hepatectomy reduces the endotoxin-induced peak circulating level of tumor necrosis factor in rats, SHOCK, vol. 5, No. 5, pp. 385-388, 1996.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, 1995.

LeNovere, N. et al., Molecular evolution of the nicotinic acetylcholine receptor: an example of multigene family in excitable cells, J. Mol. Evol., 40, pp. 155-172, 1995.

Leonard, S. et al., Neuronal nicotinic receptors: from structure to function, Nicotine & Tobacco Res. 3:203-223 (2001).

Lips et al.; Coexpression and spatial association of nicotinic acetylcholine receptor subunits alpha7 and alpha10 in rat sympathetic neurons; J.Mol.Neurosci.; 30; pp. 15-16; 2006.

Lipton, J. M. et al.; Anti-inflammatory actions of the neuroimmunomodulator ?-MSH, Immunol. Today, vol. 18, pp. 140-145, 1997.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, 1996.

Martindale: The extrapharcopoeia; 28th Ed. London; The pharmaceutical press; pp. 446-485; 1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

McGUINNESS, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, 2000.

Minnich et al.; Anti-cytokine and anti-inflammatory therapies for the treatment of severe sepsis: progress and pitfalls; Proceedings of the Nutrition Society; vol. 63; pp. 437-441; 2004.

Molina et al., CNI-1493 attenuates hemodynamic and pro-inflammatory responses to LPS, Shock, vol. 10, No. 5, pp. 329-334, Nov. 1998.

Nagashima et al., Thrombin-activatable fibrinolysis inhibitor (TAFI) deficiency is compatible with murine life, J. Clin. Invest., 109, pp. 101-110, 2002.

Nathan, C. F., Secretory products of macrophages, J. Clin. Invest., vol. 79, pp. 319-326, 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; 2001.

Noguchi et al., Increases in Gastric acidity in response to electroacupuncture stimulation of hindlimb of anesthetized rats, Jpn. J. Physiol., 46(1), pp. 53-58, 1996.

Norton, Can ultrasound be used to stimulate nerve tissue, BioMedical Engineering, 2(1), pp. 6, 2003.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.

Prystowsky, J. B. et al., Interleukin-1 mediates guinea pig gallbladder inflammation in vivo, J. Surg. Res., vol. 71, No. 2, pp. 123-126, 1997.

Pulkki, K. J., Cytokines and cardiomyocyte death, Ann. Med., vol. 29, pp. 339-343, 1997.

Rayner, S. A. et al., Local bioactive tumour necrosis factor (TNF) in corneal allotransplantation, Clin. Exp. Immunol., vol. 122, pp. 109-116, 2000.

Rinner et al.; Rat lymphocytes produce and secrete acetylcholine in dependence of differentiation and activation; J.Neuroimmunol.; 81; pp. 31-37; 1998.

Romanovsky, A. A., et al.,The vagus nerve in the thermoregulatory response to systemic inflammation, Am. J. Physiol., vol. 273, No. 1 (part 2), pp. R407-R413, 1997.

Saghizadeh et al.; The expression of TNF? by human muscle; J. Clin. Invest.; vol. 97; No. 4; pp. 1111-1116; 1996.

Saindon et al.; Effect of cervical vagotomy on sympathetic nerve responses to peripheral interieukin-1beta; Auton.Neuroscience Basic and Clinical; 87; pp. 243-248; 2001.

Saito, Involvement of muscarinic M1 receptor in the central pathway of the serotonin-induced bezold-jarisch reflex in rats, J. Autonomic Nervous System, vol. 49, pp. 61-68, 1994.

Sandborn, W. J., et al., Transdermal nicotine for mildly to moderately active ulcerative colitis, Ann. Intern. Med, vol. 126, No. 5, pp. 364-371, 1997.

Sato, E., et al., Acetylcholine stimulates alveolar macrophages to release inflammatory cell chemotactic activity, Am. J. Physiol., vol. 274, pp. L970-L979, 1998.

Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, 1999.

Scheinman, R. I., et al., Role of transcriptional activation of I?B? in mediation of immunosuppression by glucocorticoids, Science, vol. 270, pp. 283-286, 1995.

Schneider et al., High-affinity ssDNA inhibitors of the review transcriptase of type 1 human immunodeficiency virus, Biochemistry, 34(29), pp. 9599-9610, 1995.

Shafer, Genotypic testing for human immunodeficiency virus type 1 drug resistance, Clinical Microbiology Reviews, vol. 15, pp. 247-277, 2002.

Shapiro et al.; Prospective, randomised trial of two doses of rFVlla (NovoSeven) in haemophilia patients with inhibitors undergoing surgery; Thromb Haemost; vol. 80; pp. 773-778; 1998.

Sher, M. E., et al., The influence of cigarette smoking on cytokine levels in patients with inflammatory bowel disease, Inflamm. Bowel Dis., vol. 5, No. 2, pp. 73-78, 1999.

Shi et al.; Effects of efferent vagus nerve excitation on inflammatory response in heart tissue in rats with endotoxemia; vol. 15, No. 1; pp. 26-28; 2003 (Eng. Abstract).

Snyder et al., Correction of hemophilia B in canine and murine models using recombinant adeno-associated viral vectors; Nature Medicine, 5(1), pp. 64-70, Jan. 1999.

Stalcup et al., Endothelial cell functions in the hemodynamic responses to stress, Annals of the New York Academy of Sciences, vol. 401, pp. 117-131, 1982.

Steinlein, New functions for nicotine acetylcholine receptors?, Behavioural Brain Res., vol. 95, pp. 31-35, 1998.

Sternberg, E. M., Perspectives series: cytokines and the brain 'neural-immune interactions in health and disease,' J. Clin. Invest., vol. 100, No. 22, pp. 2641-2647, Dec. 1997.

Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.

Sykes, et al., An investigation into the effect and mechanisms of action of nicotine in inflammatory bowel disease, Inflamm. Res., vol. 49, pp. 311-319, 2000.

Toyabe, et al., Identification of nicotinic acetylcholine receptors on lymphocytes in the periphery as well as thymus in mice, Immunology, vol. 92, pp. 201-205, 1997.

Tracey et al., Mind over immunity, Faseb Journal, vol. 15, No. 9, pp. 1575-1576, Jul. 2001.

Tracey, K. J. et al., Anti-cachectin/TNF monoclonal antibodies prevent septic shock during lethal bacteraemia; Nature, 330: pp. 662-664, 1987.

Tracey, K. J. et al., Shock and tissue injury induced by recombinant human cachectin, Science, vol. 234, pp. 470-474, 1986.

Tracey, K.J., The inflammatory reflex, Nature, vol. 420, pp. 853-859, 2002.

Tsutsui, H., et al., Pathophysiolocical roles of interleukin-18 in inflammatory liver diseases; Immunol. Rev., 174:192-209, 2000.

Tuerk et al., RNA pseudoknots that inhibit human immunodeficiency virus type 1 reverse transcriptase; Proc. Natl. Acad. Sci. USA, 89, pp. 6988-6992, Aug. 1992.

Tuerk et al., Systematic evolution of ligands by exponential enrichment: RNA ligands to bacteriophage T4 DNA polymerase; Science, 249(4968), pp. 505-510, Aug. 3, 1990.

Van Dijk, A. P., et al., Transdermal nictotine inhibits interleukin 2 synthesis by mononuclear cells derived from healthy volunteers, Eur. J. Clin. Invest, vol. 28, pp. 664-671, 1998.

Vanhoutte, et al., Muscarinic and beta-adrenergic prejunctional modulation of adrenergic neurotransmission in the blood vessel wall, Gen Pharmac., vol. 14, pp. 35-37, 1983.

vanWesterloo, et al., The cholinergic anti-inflammatory pathway regulates the host response during septic peritonitis, The Journal of Infectious Diseases, vol. 191, pp. 2138-2148, Jun. 15, 2005.

Ventureyra, Transcutaneous vagus nerve stimulation for partial onset seizure therapy, Child's Nerv Syst, vol. 16, pp. 101-102, 2000.

Villa et al., Protection against lethal polymicrobial sepsis by CNI-1493, an inhibitor of pro-inflammatory cytokine synthesis, Journal of Endotoxin Research, vol. 4, No. 3, pp. 197-204, 1997.

Von Känal, et al., Effects of non-specific ?-adrenergic stimulation and blockade on blood coagulation in hypertension, J. Appl. Physiol., vol. 94, pp. 1455-1459, 2003.

Walland et al., Compensation of muscarinic brochial effects of talsaclidine by concomitant sympathetic activation in guinea pigs; European Journal of Pharmacology, vol. 330, pp. 213-219, 1997.

Wang et al; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waserman, S. et al., TNF-? dysregulation in asthma: relationship to ongoing corticosteroid therapy, Can. Respir. J., vol. 7, No. 3, pp. 229-237, 2000.

Watanabe, H. et al., The significance of tumor necrosis factor (TNF) levels for rejection of joint allograft, J. Reconstr. Microsurg., vol. 13, No. 3, pp. 193-197, 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183, pp. 27-31, 1995.

Watkins, L.R. et al., Implications of immune-to-brain communication for sickness and pain, Proc. Natl. Acad. Sci. U.S.A., vol. 96, pp. 7710-7713, 1999.

Webster's Dictionary, definition of "intrathecal", online version accessed Apr. 21, 2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, 1998.

Yeh, S.S. et al., Geriatric cachexia: the role of cytokines, Am. J. Clin. Nutr., vol. 70, pp. 183-197, 1999.

Zhang et al., Tumor necrosis factor, The Cytokine Handbook, 3rd ed., Ed. Thompson, Academic Press, pp. 517-548, 1998.

Cicala et al., "Linkage between inflammation and coagulation: An update on the molecular basis of the crosstalk," Life Sciences, vol. 62(20); pp. 1817-1824, 1998.

Kalishevskaya et al. "The character of vagotomy-and atropin-induced hypercoagulation," Fizio. Zh SSSR Im I M Sechenova, 65(3): pp. 398-404, 1979.

Khatun, S., et al., "Induction of hypercoagulability condition by chronic localized cold stress in rabbits," Thromb. and Haemost., 81: pp. 449-455, 1999.

Kudrjashov, et al. "Reflex nature of the physiological anticoagulating system," Nature, vol. 196(4855): pp. 647-649; 1962.

Kuznik, et al., "Secretion of blood coagulation factors into saliva under conditions of hypo-and hypercoagulation," Voprosy Meditsinskoi Khimii, vol. 19(1): pp. 54-57; 1973.

Kuznik, et al., "Heart as an efferent regulator of the process of blood coagulation and fibrinolysis," Kardiologiia, vol. 13(3): pp. 10-17, 1973.

Kuznik, et al., "Blood Coagulation in stimulation of the vagus nerve in cats," Biull. Eskp. Biol. Med., vol. 78(7): pp. 7-9, 1974.

Kuznik, et al., "The role of the vascular wall in the mechanism of control of blood coagulation and fibrinolysis on stimulation of the vagus nerve," Cor Vasa, vol. 17(2): pp. 151-158, 1975.

Kuznik, et al., "The dynamics of procoagulatible and fibrinolytic activities during electrical stimulation of peripheral nerves," Fizio. Zh SSSR Im I M Sechenova, 3: pp. 414-420, 1979.

Lang, et al., "Neurogienic control of cerebral blood flow," Experimental Neurology, 43: pp. 143-161, 1974.

Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.

Mishchenko, et al., "Coagulation of the blood and fibrinolysos in dogs during vagal stimulation," Fizio. Zh SSSR Im I M Sechenova, vol. 61(1): pp. 101-107, 1975.

Von Känal, et al., Effects of sympathetic activation by adrenergic infusions on hemostasis in vivo, Eur. J. Haematol., vol. 65: pp. 357-369, 2000.

Cohen, "The immunopathogenesis of sepsis," vol. 420(19): pp. 885-891, 2002.

Weiner, et al., "Inflammation and therapeutic vaccination in CNS diseases," vol. 420(19): pp. 879-884, 2002.

Benoist, et al., "Mast cells in autoimmune disease" vol. 420(19): pp. 875-878, 2002.

Payne, J. B. et al., Nicotine effects on PGE2 and IL-1 beta release by LPS-treated human monocytes, J. Perio. Res., vol. 31, No. 2, pp. 99-104, 1996.

Pullan, R. D., et al., Transdermal nicotine for active ulceratiive colitis, N. Engl. J. Med., vol. 330, No. 12, pp. 811-815, 1994.

Takeuchi et al., A comparision between chinese blended medicine "Shoseiryuto" tranilast and ketotifen on the anit-allergic action in the guinea pigs, Allergy, vol. 34, No. 6, pp. 387-393, 1985 (eng. abstract).

Faltys et al.; U.S. Appl. No. 12/797,452 entitled "Nerve cuff with pocket for leadness stimulator," filed Jun. 9, 2010.

Hatton et al.; Vagal nerve stimulation: overview and implications for anesthesiologists; Int'l Anesthesia Research Society; vol. 103; No. 5; pp. 1241-1249; Nov. 2006.

Hoffer et al.; Implantable electrical and mechanical interfaces with nerve and muscle; Annals of Biomedical Engineering; vol. 8; pp. 351-360; 1980.

Krarup et al; Conduction studies in peripheral cat nerve using implanted electrodes: I. methods and findings in controls; Muscle & Nerve; vol. 11; pp. 922-932; Sep. 1988.

Loeb et al.; Cuff electrodes for chronic stimulation and recording of peripheral nerve activity; Journal of Neuroscience Methods; vol. 64; pp. 95-103; 1996.

Strojnik et al.; Treatment of drop foot using and implantable peroneal underknee stimulator; Scand. J. Rehab. Med.; vol. 19; pp. 37R43; 1987.

Beliavskaia et al.,"On the effects of prolonged stimulation of the peripheral segment of the vagus nerve on blood clotting time under different bodily conditions," Fiziologicheskii Zhurnal SSSR Imeni I.M. Sechenova., vol. 52(11); p. 1315-1321, Nov. 1966.

Kalishevskaya et al.; Neural regulation of the fluid state of the blood; Usp. Fiziol. Nauk;,vol. 13; No. 2; pp. 93-122; 1982.

Kuznik, et al., "Role of the heart and vessels in regulating blood coagulation and fibrinolysis," Kagdiologiia, vol. 13(4): pp. 145-154, 1973.

Kuznik, "Role of the vascular wall in the process of hemostatis," Usp Sovrem Biol., vol. 75(1): pp. 61-85, 1973.

Pateyuk et al.,"Treatment of Botkin's disease with heparin," Klin. Med., 1 vol. 51(3): pp. 113-117, 1973.

Sokratov, et al. "The role of choline and adrenegic structures in regulation of renal excretion of hemocoagulating compounds into the urine," Sechenov Physiological Journal of the USSR, vol. 63(12): pp. 1728-1732, 1977.

Zitnik et al.; U.S. Appl. No. 12/874,171 entitled "Prescription pad for treatment of inflammatory disorders," filed Sep. 1, 2010.

Levine, Jacob A.; U.S. Appl. No. 13/338,185 entitled "Modulation of sirtuins by vagus nerve stimulation" filed Dec. 27, 2011.

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.

Tracey, K. J. et al., Physiology and immunology of the cholinergic antiinflammatory pathway; J Clin Invest.; vol. 117: No. 2; pp. 289-296; Feb. 2007.

Van Der Horst et al.; Stressing the role of FoxO proteins in lifespan and disease; Nat Rev Mol Cell Biol.; vol. 8; No. 6; pp. 440-450; Jun. 2007.

Westerheide et al.; Stress-inducible regulation of heat shock factor 1 by the deacetylase SIRT1.; Science; Vo. 323; No. 5717; pp. 1063-1066; Feb. 2009.

Nadol et al., "Surgery of the Ear and Temporal Bone," Lippinkott Williams & Wilkins, 2nd Ed., 2005, (Publication date: Sep. 21, 2004), p. 580.

Levine et al.; U.S. Appl. No. 13/467,928 entitled "Single-Pulse Activation of the Cholinergic Anti-Inflammatory Pathway to Treat Chronic Inflammation," filed May 9, 2012.

US 6,184,239, 02/2001, Puskas (withdrawn)

* cited by examiner

FIG. 1: Artifact-guided placement and programming of percutaneous electrode leads

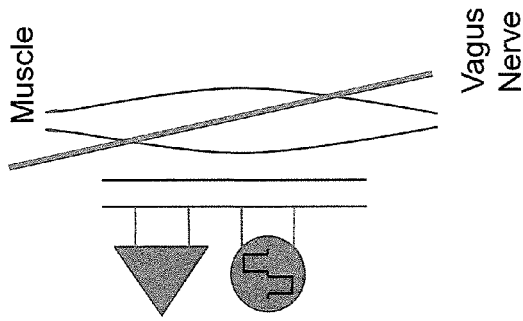

- Problem
  - Efficacious stimulation without side-effects (may not be a problem if stimulation thresholds are extremely low).

- Observations
  - Artifact (i.e., muscle twitching) was the most significant problem while stimulating rats. Problems were resolved by repositioning electrode.
  - Anecdotal evidence claims that artifact is a significant problem with percutaneous insertions and requires significant "tweaking" to get efficacious stimulation of vagus (VNS).

- Proposed System
  - EMG artifact can be used to indicate stimluation artifact while surgeon inserts electrode allowing placement optimization.
  - Quadrapolar contacts allow 6 contacts to be evaluated for minimal artifact during programming.
  - Could be used for placement of electrode for any minimally invasive surgical technique for stimulators including VNS.

FIG. 3: Artifact Guided System Placement and Programming

- Surgical Methodology
  - Pulse electrode pairs at 1-10 Hz and measure EMG (& ECG) between pulses
  - Test all 6 combinations and provide surgeon with real-time artifact factor

- Programming Methodology
  - Run EMG (& ECG) and provide clinician prioritized list of contact combinations from best to worst, also can be used to find optimum pulse width

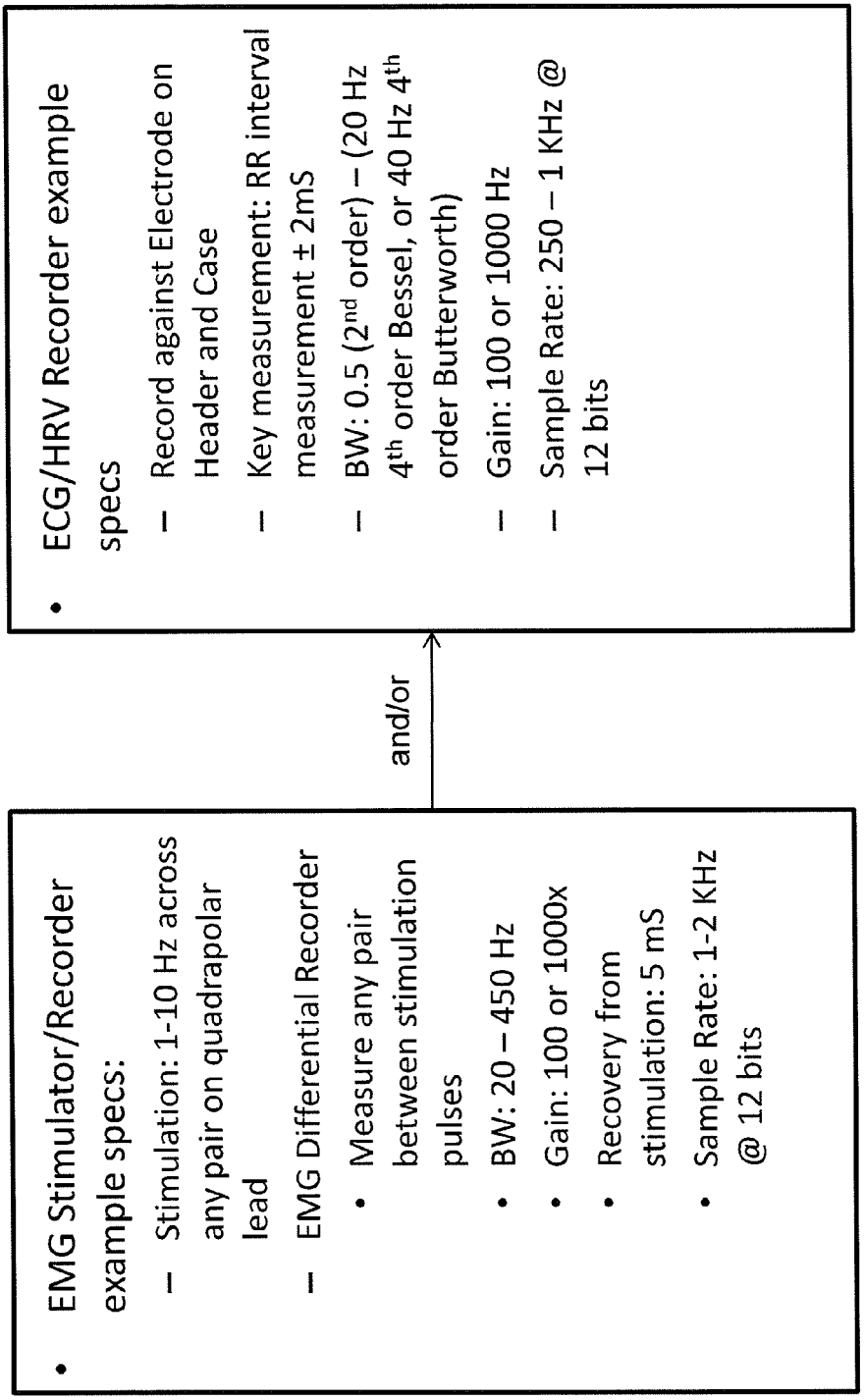
FIG. 4: Artifact Guided Positioning System Specifications

FIG. 5: Artifact Types and Measurement Techniques

| Artifact | Measurement | Mechanism |
|---|---|---|
| Muscle (e.g., twitch) | Evoked EMG | Collateral current spread to muscles and nerves |
| Sensation/Pain | Patient Feedback | Collateral current spread to nerves |
| Vagal Bradycardia, atrio-ventribular block, ventricular asystole | ECG: Instantaneous Heart Rate (IHR), Heart Rate Variability (HRV) | Stimulation of non-targeted vagal fibers |
| Voice/Hoarseness/Cough | Patient Feedback | Stimulation of non-targeted vagal fibers |
| Paresthesia | Patient Feedback | |
| Dyspnea | Respiratory Monitoring | Stimulation of Carotid bodies, arterial baroreceptors and cardiac C-Fibers |
| Gastro-intestinal motility | Gastric Acid Monitoring | Stimulation of non-targeted vagal fibers |
| Fever | Temperature | |
| Hypertension | Heart Rate Variability, Arterial pressure | Stimulation of Carotid bodies, arterial baroreceptors and cardiac C-Fibers |

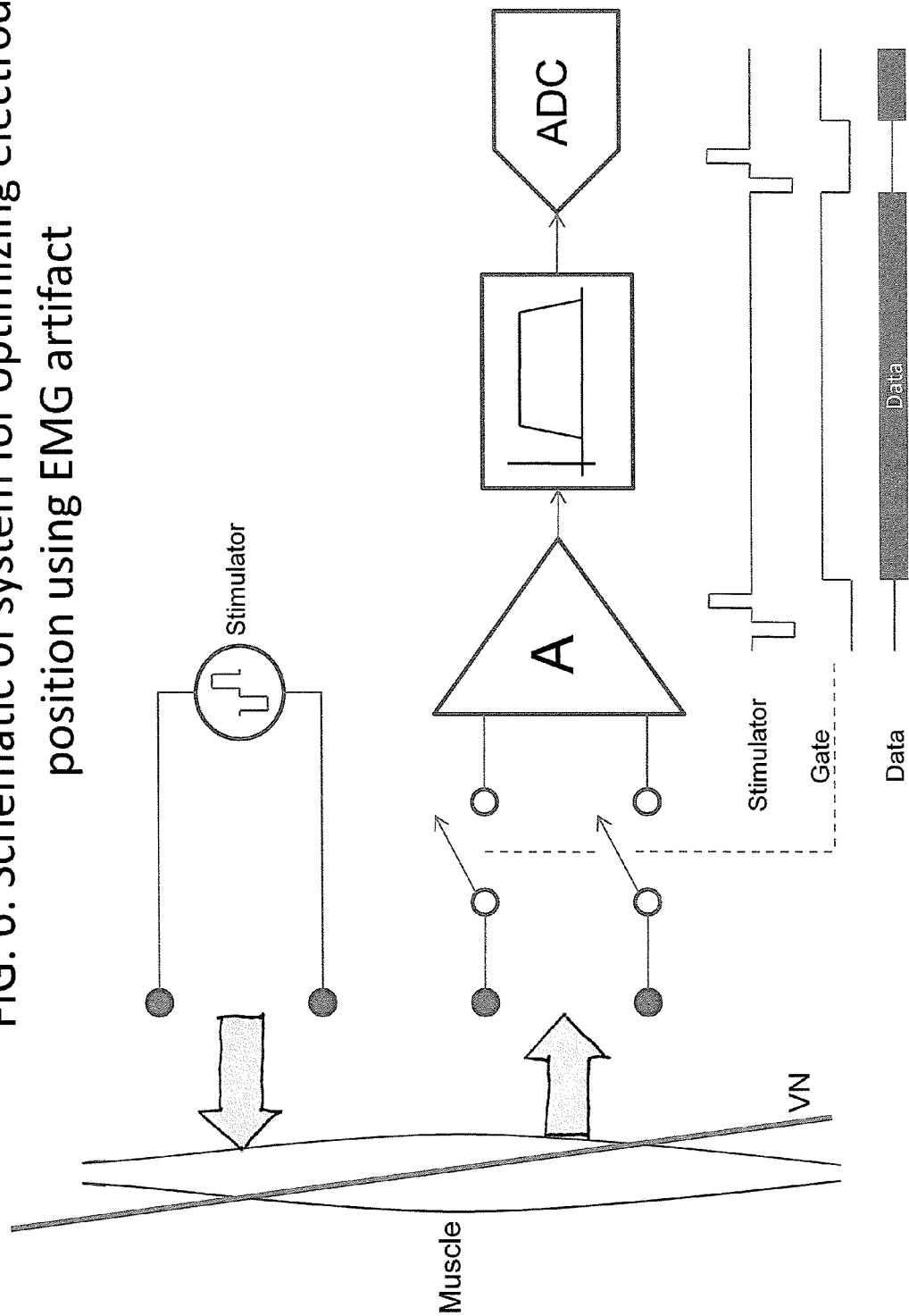
FIG. 6: Schematic of system for optimizing electrode position using EMG artifact

US 8,412,338 B2

DEVICES AND METHODS FOR OPTIMIZING ELECTRODE PLACEMENT FOR ANTI-INFLAMATORY STIMULATION

CROSS-REFERENCE TO RELATED APPLICATIONS

This application claims the benefit under 35 U.S.C. 119 of U.S. Patent Application No. 61/115,806 filed Nov. 18, 2008, titled "DEVICES AND METHODS FOR OPTIMIZING ELECTRODE PLACEMENT FOR ANTI-INFLAMMATORY STIMULATION".

INCORPORATION BY REFERENCE

All publications and patent applications mentioned in this specification are herein incorporated by reference in their entirety as if each individual publication or patent application was specifically and individually indicated to be incorporated by reference.

BACKGROUND OF THE INVENTION

Inflammation is a complex biological response to pathogens, cell damage, and/or biological irritants. Inflammation may help an organism remove injurious stimuli, and initiate the healing process for the tissue, and is normally tightly regulated by the body. However, inappropriate or unchecked inflammation can also lead to a variety of disease states, including diseases such as hay fever, atherosclerosis, arthritis (rheumatoid, bursitis, gouty arthritis, polymyalgia rheumatic, etc.), asthma, autoimmune diseases, chronic inflammation, chronic prostatitis, glomerulonephritis, nephritis, inflammatory bowel diseases, pelvic inflammatory disease, reperfusion injury, transplant rejection, vasculitis, myocarditis, colitis, etc. In autoimmune diseases, for example, the immune system inappropriately triggers an inflammatory response, causing damage to its own tissues.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

The nervous system, and particularly the Vagus nerve, has been implicated as a modulator of inflammatory response. The Vagus nerve is part of an inflammatory reflex, which also includes the splenic nerve, the hepatic nerve and the trigeminal nerve. The efferent arm of the inflammatory reflex may be referred to as the cholinergic anti-inflammatory pathway. For example, Tracey et. al., have previously reported that the nervous system regulates systemic inflammation through a Vagus nerve pathway. This pathway may involve the regulation of inflammatory cytokines and/or activation of granulocytes. Thus, it is believed that appropriate modulation of the Vagus nerve (or other portions of the inflammatory reflex) may help regulate inflammation. Inhibition of the inflammatory reflex is described more fully in U.S. Pat. No. 6,610,713, filed on May 15, 2001 and titled "INHIBITION OF INFLAMMATORY CYTOKINE PRODUCTION BY CHOLINERGIC AGONISTS AND VAGUS NERVE STIMULATION"; pending U.S. patent application Ser. No. 11/807,493, filed on Feb. 26, 2003 and titled "INHIBITION OF INFLAMMATORY CYTOKINE PRODUCTION BY STIMULATION OF BRAIN MUSCARINIC RECEPTORS"; pending U.S. patent application Ser. No. 10/446,625, with a priority date of May 15, 2001 and titled "INHIBITION OF INFLAMMATORY CYTOKINE PRODUCTION BY CHOLINERGIC AGONISTS AND VAGUE NERVE STIMULATION"; and pending U.S. patent application Ser. No. 11/318,075, filed on Dec. 22, 2005 and titled "TREATING INFLAMMATORY DISORDERS BY ELECTRICAL VAGUS NERVE STIMULATION." This provisional patent application may also be related to pending U.S. Provisional Patent Application Ser. No. 60/968,292, titled "DEVICES AND METHODS FOR INHIBITING GRANULOCYTE ACTIVATION BY NEURAL STIMULATION", and Ser. No. 60/982,681, titled "TRANSCUTANEOUS VAGUS NERVE STIMULATION REDUCES SERUM HIGH MOBILITY GROUP BOX 1 LEVELS AND IMPROVES SURVIVAL IN MURINE SEPSIS". Each of these patent and pending applications is herein incorporated by reference in its entirety.

A system for stimulating one or more nerves of the inflammatory reflex may include one or more electrical leads which may be implanted acutely or chronically, and may be positioned adjacent or in contact with the Vagus nerve or other nerves of the inflammatory reflex, and particularly the cholinergic anti-inflammatory reflex.

Unfortunately, stimulation of the inflammatory reflex is made difficult by artifacts and/or side-effects of stimulation. Most stimulation (neurostimulation) devices target neurons or muscles with electrodes that generate current to activate these organs. Ideally, such devices should stimulate only the target tissue or organ. Even more ideally, the stimulation of the target should be precise enough to avoid collateral stimulation. Furthermore, the stimulation should evoke the desired effect, without triggering other effects. In practice, localized stimulation has proven very difficult, and practically unrealizable. Unintentional stimulation of collateral organs from non-specific electrodes can be detrimental enough to prevent treatment and/or reduce the efficacy of treatment by requiring suboptimal stimulation.

Furthermore, the in-vivo stimulation environment may be very non-homogenous in electrical conductivity and organ activation characteristics (e.g. fiber diameter). The practical significance of this non-homogeneity is that positional changes in the stimulating electrodes can shift the path of the activating current, or change the characteristics of the stimulating current itself, such as the pulse width, rate, polarity, asymmetry, or the like. Control of electrode position and stimulation current characteristics is therefore critical for the success of neurostimulation therapies, particularly those in which collateral stimulation is an issue. Described herein are device and methods for optimal positioning of the electrode during surgery and optimization of stimulation parameters.

Currently available systems for stimulating nerves of the inflammatory reflex such as the Vagus nerve are generally not appropriate for stimulation of the Vagus nerve to regulate inflammation, because they would either be ineffective for inhibiting inflammation, or because they would result in undesirable side-effects. The configuration of the electrodes and stimulators, including the configuration of the stimulating electrodes of the electrical leads, in conjunction with the level, duration and frequency of stimulation, are critical to inhibiting or modulation of the inflammatory response appropriately (e.g., without desensitizing the inflammatory reflex).

For example, US Patent Application publication numbers 2006/0287678, US 2005/0075702, and US 2005/0075701 to Shafer describe a device and method of stimulating neurons of the sympathetic nervous system, including the splenic nerve to attenuate an immune response. Similarly, US Patent Application publication numbers 2006/0206155 and 2006/010668 describe stimulation of the Vagus nerve by an implanted electrode. US Patent Application publication number 2007/0027499 describes a device and method for treating mood disorders using electrical stimulation. US Patent Application publication number 2006/0229677 to Moffitt et al. describes transvascularly stimulating a nerve trunk through a blood vessel. U.S. Pat. No. 7,269,457 to Shafer et al. also describes a system for vagal nerve stimulation with multi-site cardiac pacing. All of these published patent applications and issued patents describe systems and methods for stimulating nerves, including the Vagus nerve. However, none of these publications teach or suggest stimulating the inflammatory reflex, including the Vagus nerve, using a system or method that would prevent desensitization of the inflammatory reflex, and would avoid undesirable effects or artifacts, such as muscle twitch or seizures, pain, cardiac effects (e.g., increase heart rate, etc.), hoarseness, or the like.

In practice, when a surgeon is inserting an electrode, the position of the electrode is necessarily crude, since implantation is often done via catheter or other minimally-invasive techniques, or done using indirect imaging techniques. Thus, it is often difficult for a doctor to precisely implant an electrode. In addition, we have found that the correct placement of an electrode may vary based on patient variability. This means that what an optimal position in one patient (e.g., a certain proximity to the vagus nerve) may be sub-optimal or non-functional in another patient. Thus, although stimulation systems, including those described above, may be applied by a surgeon using a known protocol, such insertion does not usually result in minimal stimulation artifact, particularly relative to the desired effect. To correct for this, stimulation levels may simply be increased (e.g., increasing the intensity or frequency) to attain a desired stimulation, often at the expense of an increased artifact or side-effect. Further, even when a stimulation electrode is implanted using a "trial and error" technique, it may be overly difficult or costly to examine the stimulation artifact in determining the optimal position, particularly in any reliable, reproducible manner.

Thus, there is a need for electrical leads and systems that include electrical leads are configured to appropriately modulate the inflammatory reflex without causing undesirable side effects or artifacts due to the stimulation.

SUMMARY OF THE INVENTION

Described herein are systems, devices and methods for optimizing the position of electrodes for stimulating the inflammatory reflex to inhibit or otherwise modulate inflammation. In particular, described herein are systems, devices and methods for optimizing the position of one or more electrodes relative to one or more portion of the inflammatory reflex, such as the vagus nerve, the splenic nerve, the hepatic nerve and the trigeminal nerve.

In some variations, the position of the stimulation electrode (or electrodes) is optimized by detecting and/or measuring "stimulation artifacts" during insertion/implantation and programming of the electrode. Certain of the devices, systems and methods allow for the feedback of information to the clinician or to an analysis device in real-time during or after implantation. Stimulation artifact is broadly defined as a signal or signals resulting from the electrode that is not part of the desired stimulation. For example, stimulation artifact may be electrical (e.g., ECG, EKG, EMG), muscle twitch, cramping, seizure, cardiac effects (heart rate variability, increase in heart rate, decrease in heart rate, etc.), or other undesirable effects, as described further below. Thus, the systems and methods described herein may include one or more sensors for detecting and/or measuring such stimulation artifact, and may further include the display and or analysis of this artifact. Information from certain of the stimulation artifact may be used to position the electrode, and/or to choose which electrodes on a device to use for stimulation.

In some variations, the stimulation artifact can be detected from the same electrodes that are applying stimulation, or from different electrodes on the same lead. The artifact can also be measured by a distant electrode/lead. The artifact can be measured simultaneously with applied stimulation, and/or it can be measured between stimulation pulses. Measured artifact can consist of any appropriate electrical phenomena such as EMG, EKG, EEG, and/or evoked potentials such as those evoked to or from a target organ such as the Spleen. Other sensors can be used to detect stimulation artifact, including temperature sensors, tissue resistance sensors, and chemical sensors.

In addition to sensing and/or measuring artifact to optimize electrode placement, the target devices, systems and methods described herein may also be used to maximize the target response and minimize artifact response (e.g. minimization of heart rate and maximization of splenic evoked potential).

Generally, separating a stimulation artifact from a stimulation is complicated by the fact that a stimulus is usually much larger than an evoked intentional or artifact signal. Several mechanisms are described herein to facilitate measurement in these conditions including: high bandwidth fast recovery amplifiers, analog gating signals, digital gating, signal processing such as averaging and autocorrelation.

In addition to the methods and devices for optimizing the position of the electrode, stimulation artifact may be controlled by optimizing the type of electrode and/or the stimulation parameters. For example, the electrode (or electrodes) used may be configured to optimize simulation of a portion f the inflammatory reflex (such as the vagus nerve, the splenic nerve, the hepatic nerve and the trigeminal nerve). In some variations, the level of stimulation applied may be particularly important to avoid overstimulation (e.g., desensitization) of the inflammatory reflex, preventing inhibition (or long-lasting inhibition) of the inflammatory reflex. For example, the intensity (voltage and/or current level), duration, frequency, or the like, may be optimized. Low-intensity or particularly infrequent stimulation may be particularly important. Any of the methods, devices and systems for optimizing position of the stimulation electrodes may also be used in conjunction with any of the optimized electrodes and/or stimulation protocols, or methods of optimizing the electrodes and/or stimulation protocols. In practice, the position of the electrode may be fundamental.

In general, the methods described herein include the real-time monitoring of one or more 'artifacts' during implantation. In some variations, the artifact monitored may be averaged. For example, EMG signals (muscle response) may be monitored. In some variations, EKG (e.g., from the chest) may also be used to measure changes in heart rate (e.g., heart rate variability). Changes in heart rate may be used to both confirm position relative to a portion of the inflammatory reflex such as the vagus nerve, and may also be used to determine undesirable artifact. In some variations, evoked potentials from either the target nerve (e.g., vagus nerve, splenic nerve, hepatic nerve, trigeminal nerve, etc.) or from nearby or adjacent nerves that are not part of the inflammatory reflex, may be monitored as stimulation artifact.

For example, a neuron may be stimulated using an implanted electrode in a first position, and the evoked potentials may be monitored as they propagate from the implantation site of the nerve. Multiple simulations can be performed and the evoked responses in one or more nerves (either target and/or non-target nerves) be averaged over these multiple stimulations. Monitoring the evoked potential may allow confirmation that the nerve is being stimulated, and that adjacent nerves are not being stimulated.

In one variation, a monitoring sensor (e.g., electrode) is used to detect stimulation artifact. In some variations, multiple modalities of artifact may be measured and used to optimize the position. For example, a first artifact modality may be EMG or muscle twitch. The measurement of EMG or muscle twitch may be measured off of one or more pair of the multipolar probe applying the stimulus. Thus, the EMG artifact may be measured near the location of the stimulation (e.g., the neck). A second artifact modality may be EKG, which may be used to measure one or more component of the cardiac cycle (e.g., heart rate, etc.). The same electrode or different electrodes may be used to measure EKG (e.g., chest electrodes). A third artifact modality (e.g., evoked potentials, or compound action potentials) may be measured. In practice, any combinations of these artifact modalities may be used, and they may be weighted. For example, the EMG or muscle twitch artifact may be weighted more than the EKG artifact (or vice versa).

Any appropriate type of stimulation electrode may be used, include one or more of a field effect electrode, multi-polar (e.g., bipolar, octopolar), cuff electrodes, hook electrodes, or the like. The techniques described herein are particularly useful for field effect electrodes whose position may be adjusted during surgery, or any probe including multiple contacts, or any stimulator that may be adjusted to modify the stimulation parameter (e.g., intensity, etc.).

Also described herein are amplifiers that are adapted to detect and/or measure one or more of these artifacts relative to the stimulation. For example, the stimulation (which is typically a high intensity signal), must be isolated appropriately from the relatively low-intensity stimulus artifact. For example, an amplifier may include a fast recovery amplifier that clamps the stimulus (e.g., 20 mV stimulus), so that the low-intensity response (stimulus artifact such as EMG). The amplifier may also include appropriate averaging capability that averages the artifact following the stimulation. The system may use this information to generate a metric, such as artifact power. For example, artifact power may be a measure of the total power (e.g., the area under the waveform) of the artifact measured. The electrodes may be placed or selected to minimize a metric such as artifact power. In one variation, the system includes a probe having multiple electrode pairs, and is configured to include an output of artifact power for each of the pairs.

In some variations, the optimization of electrode position includes the measurement of stimulation artifact between stimulation pulses. For example, the stimulation electrodes may be configured to both apply a stimulation signal and to detect an electrical signal. Electrical signals detected from these electrodes may be analyzed (e.g., by sending to an analysis module) to remove the stimulation and analyze any electrical signal between periods of stimulation. For example, the electrical signal measured from the electrodes may be locked with the stimulation signal so that it can be subtracted or gated to remove the stimulation signal from the received signal. Thus, the analysis module may block out the relatively high-intensity applied signal and amplify the relatively low-intensity recorded signal. The signal may be further filtered or conditioned. For example, when using an EMG stimulus artifact, the signal may be filtered at 20-450 Hz, a spectral range that may provide useful information when EMG is used. If the stimulus artifact measured is heart rate variability, the signal may be filtered to pass within the spectral range of 0.5 to 20 Hz.

In addition to measuring stimulation artifact, the system may also measure the desired effect, including one or more indicators of the inhibition of inflammation. For example, the system may include one or more sensors to detect and/or measure inhibition of inflammation based on body temperature, distribution of cell types (e.g., granulocyte distribution), levels of certain neurotransmitters (e.g., acetylcholine), and/or markers of inflammation such as CD11, etc. The system may thus be configured to optimize position based on either or both the artifact signal (e.g., muscle twitch, heart rate, nerve firing, etc.) and/or based on the desired signal (e.g., inhibition of inflammation).

BRIEF DESCRIPTION OF THE DRAWINGS

FIG. 1. Illustrates the justification and hypothesis of artifact-guided placement and programming of percutaneous electrode leads.

FIG. 3 shows a schematic of one variation of an artifact-guided placement system (a system for optimizing the placement of one or more electrodes).

FIG. 4 illustrates one variation of schematics for an artifact-guided placement system as described herein.

FIG. 5 is a table of variations of artifacts that may be monitored as part of the placement systems described herein.

FIG. 6 is a partial schematic of one variation of a system for optimizing position using EMG artifact.

DETAILED DESCRIPTION OF THE INVENTION

Figure 2:
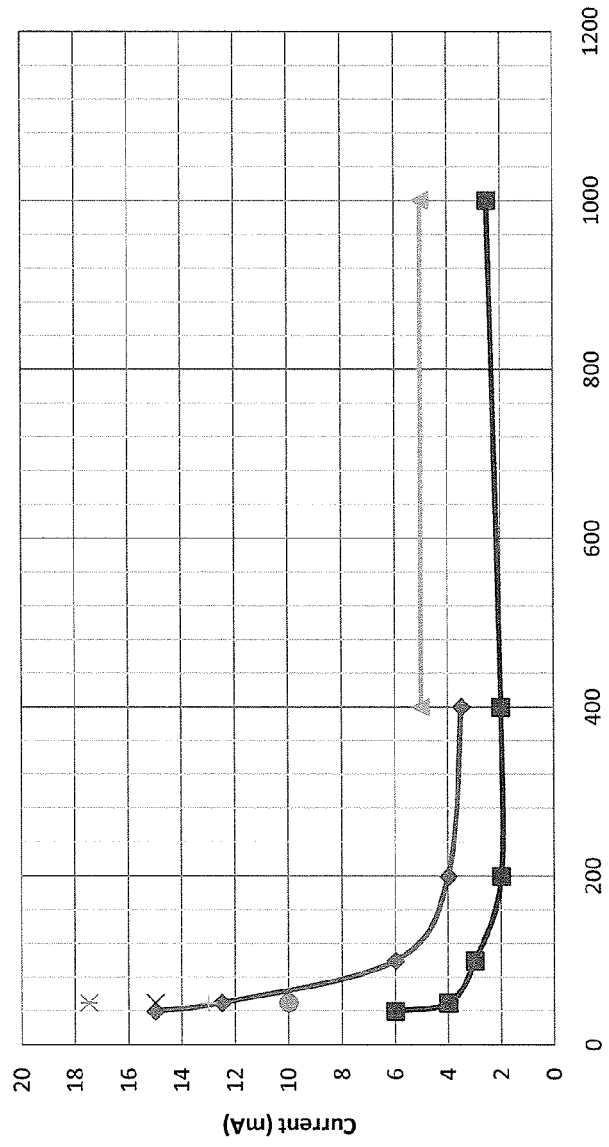
FIG. 2 shows a strength-duration curve for a Rat stimulated at various (labeled) protocols.

Described herein are devices, systems, and methods for optimizing placement of one or more electrodes. For example, the position may be optimized to stimulate the inflammatory reflex and thereby inhibit inflammation, while minimizing or eliminating undesirable side effects. Side effects may include cardiac effects (depression or acceleration of heart rate, blood pressure or the like), dry mouth, muscle twitching or spasm, etc. Such side effects may result from stimulation artifacts, which may occur when stimulating nearby muscle, nerve or other organs, or may occur because of overstimulation. Although the devices, systems and methods for optimizing position described herein are primarily directed to optimizing stimulation of the inflammatory reflex (e.g., the vagus nerve), some of the devices, system and methods described herein may also be used to optimize the position of other body regions or systems.

As illustrated in FIG. 1, preliminary studies in rats using various electrode types (hook, field effect, and sheath cuff electrodes) implanted for stimulation of the vagus nerve, in order to inhibit inflammation via the inflammatory reflex. FIG. 1 describes the problem address by the devices, systems and methods for optimizing placement of electrodes (leads) for stimulation. Based on preliminary experiments, the most significant problem while stimulating in rats is the side effect of muscle twitching. Muscle twitching may occur because of the undesirable stimulation of nearby muscle fibers or nerves innervating muscle fibers. This stimulation artifact may be reduced by changing the position of the electrode. This is consistent with other anecdotal reports from implantation of nerve stimulation, in which the percutaneous insertion of electrodes requires significant manual tweaking or adjustment of individual electrodes to get efficacious stimulation (e.g., vagus stimulation or "VNS"). FIG. 2 shows strength duration curves from this preliminary rat study.

As mentioned briefly above, a system may include an electrode (or electrode lead having multiple electrodes), a stimulator (for applying energy from the electrode(s)), a controller (for controlling stimulation and/or optimization), and an analysis module for receiving input from the controller (and the electrode and/or other sensors) and detecting and analyzing the stimulation artifact due to the stimulation. The analysis module may be a separate component, or it may be part of the controller. The system may also include one or more additional sensors for detecting stimulation artifact. In some variations, the system also includes an output (e.g., a display, one or more LEDs, an audible output, a wireless output for communication with a computer, etc.), for presenting an index or factor of the artifact (such as the artifact power) for the electrode(s).

FIG. 3 illustrates one variation of a schematic for a method for optimizing electrode position based on feedback from stimulation artifact ("artifact guided placement and programming"). In FIG. 3, two components, surgical and programming, contribute to the method and system for optimizing electrode position. For example, the surgical methodology may include implanting a multipolar electrode (e.g., an octopolar electrode) adjacent to a subject's vagus nerve in the region of the subject's neck. The electrode lead (containing multiple electrodes) may be secured in a first position using one or more locking/unlocking anchors. In some variations, the lead is secured in position so that it can later be repositioned incrementally, or completely removed. In some variations, the lead is secured so that it does not substantially move (or allow slight adjustments). A re-positionable anchor may allow the lead to be implanted, held in a first position, and then adjusted to a second position, where it can again be locked in place. For example, the lead may include a re-positionable anchor that includes a plurality of retractable tines which may releasably engage the tissue. In some variations, the lead may include an inflatable/deflatable region. Other variations of locking/unlocking anchors may be used in embodiments allowing repositioning of the lead.

In some variations, the electrode or electrode lead used may be configured for both applying energy to inhibit the inflammatory reflex (e.g., by stimulating the vagus nerve) and for receiving a signal representative of the stimulation artifact (e.g., EMG, EKG, evoked potentials, etc.). In some variations the lead includes processing (e.g., filters, amplifiers, etc.) that facilitate this.

Once the multiple-electrode lead is implanted, various combinations of electrode pairs may be tested. For example, as shown in FIG. 3, pulsed electrode pairs (e.g., at 1-10 Hz) may be applied sequentially between different pairs of the electrodes, and the artifact measured (e.g., EMG, ECG, etc.) during the duration between stimulation. The artifact may be correlated to the stimulation pair so that an index (e.g., artifact power) may be calculated for each electrode pair. For example, for a six-electrode pair lead, all six combinations of electrodes may be tested, and a real-time artifact factor or index, such as artifact power, may be provided to the doctor, allowing her to determine which pair has the lowest stimulation artifact and/or allowing repositioning of the electrode. In this way an optimal pair of electrodes (or single electrode when monopolar stimulation is used) may be determined. The system may allow the optimal electrode(s) to be recorded or chosen by the system, so that further stimulation of the subject (after the optimizing stage) may be performed using this optimal electrode/electrode pair.

The system may include instructions (e.g., programming) for evoking and analyzing the artifact associated with the electrode(s). For example, the controller and/or analysis module may include instructions for filtering a signal received after application of the stimulation in order to determine the signaling artifact (e.g., evoked potential, EKG, EMG). In some variations, the programming may also determine an index representing the artifact. For example, artifact power corresponding to a particular electrode or set of electrodes may be determined by detecting and/or measuring the signal following stimulation from a particular electrode or pair of electrodes. The signal may be filtered to remove the stimulation pulse(s), and may be bandwidth filtered to a particular region of interest (e.g., 20-450 Hz or other range relevant to EMG, 0.5 to 20 Hz or other range relevant to heart rate variability, etc.). Averaging across multiple stimulations may also be performed, and the controller and/or analysis module may include instructions determining the appropriate averaging to be performed (and/or number of stimulations to be performed to achieve an acceptable result).

For example, in some variations, the system outputs an "artifact power" for the electrode(s). In some variations, the artifact power is the index of the stimulation artifact that is calculated from the area under the curve of the stimulation artifact. Other means of quantifying the stimulation artifact associated with an electrode may also be used. In some variations, the index for each electrode includes an indication of the magnitude of the desired effect (e.g., stimulation of the inflammatory reflex, inhibition of inflammation, etc.). The module may include inputs from one or more sensors, in addition to the electrode(s), and may use all or a subset of these inputs to determine the index.

As mentioned, the systems, devices and methods may both help optimize the position of the one or more electrodes and/or may help optimize the selection of one or more electrodes from a multi-electrode lead.

FIG. 4 shows a schematic of another variation (indicating exemplary parameters) of a system for optimizing electrode position. Two artifact modalities may be used. The primary modality is EMG and the secondary modality is ECG (and specifically, heart rate variability or HRV). In FIG. 4, the system provides a 1-10 Hz stimulation across any or all of the electrodes of a multi-electrode lead. The same electrodes applying the stimulation may be used to record the stimulation artifact immediately post-stimulation, as mentioned above. The post-stimulation (artifact) signal may be measured between stimulation pulses; in this example the artifact modality is EMG, and the stimulation artifact signal is filtered at a bandwidth of 20-450 Hz, and amplified to a gain of 100 or 1000×. The system is configured to have a rapid recovery from the stimulation of approximately 5 ms, and a sample rate for detecting the stimulation artifact of approximately 1-2 Hz at 12 bits. As mentioned, the sampling processing may occur at the level of the electrode(s), the controller, the analysis module, or any other appropriate portion of the system. The signal received may be recorded and stored, and may be used to average with other signals, or may be used for further processing (e.g., calculation of an index).

The second artifact modality which may additionally be used in the example shown in FIG. 4 is the ECG modality. In particular, in this example, the heart rate variability is used. For example, the heart rate variability is recorded against an electrode on the probe and an additional electrode (e.g., reference electrode) elsewhere on the subject's body. Any other appropriate sensor input may be used, including a traditional chest/skin ECG electrode. The system may measure the RR interval from the ECG (e.g., within plus/minus 2 ms), and may filter the artifact signal received using a bandwidth of about 0.5 and about 20 Hz, as indicated. The signal may also be amplified by 100 or 1000x, and the sample rate may be between about 250 and 1 KHz at 12 bits.

As illustrated above, in some variations, the system monitors EMG (and/or ECG) between stimulation pulses, allowing a surgeon to place and program electrode objectively to reduce artifact. Thus, the system may provide on-the-fly (e.g., real-time or semi-real time) indicators of an indicator or artifact (and/or artifact plus efficacy of target stimulus). This may help avoid risk when implanting and stimulating a subject, by reducing the reliance on the doctor's skill and experience. Preliminary animal tests may show whether the system or just electrode type is the dominate factor and potentially help select electrode types, and may also show whether the desired stimulation effect (e.g., TNF levels) and the artifact thresholds are independent or correlated.

As mentioned above, any appropriate artifact modality may be used. FIG. 5 illustrates some of the more common artifact modalities that may be used, particularly those useful for positioning or selecting electrodes for stimulating the inflammatory reflex. The "measurement" column indicates one way that the artifact modality may be measured. Other variations are intended to be incorporated. The "mechanism" column suggests some ways in which these artifacts may arise due to stimulation from electrodes targeting the inflammatory reflex.

FIG. 6 schematically illustrates another example of a system for optimizing electrode position using stimulation artifact. In this example, the artifact modality is EMG. On the left of the figure, a muscle is illustrated in relation to one portion of the inflammatory reflex, the vagus nerve (VN). In this example, the application of stimulation intended to reach the vagus nerve (from the stimulator on top, may result in collateral stimulation of the muscle, which may be detected. The module indicated on the lower right portion of the figure indicates one manner in which this stimulation artifact may be detected and thus analyzed. In FIG. 6, electrical signals from the muscle (EMG signal) are gated against the stimulation impulse to remove the high-level stimulation signal from the artifact signal. A bandwidth filter is further used to focus the spectrum of the artifact signal to a smaller region (e.g., the range particularly relevant to EMG signals), and may be amplified (resulting in the "data" indicated). The signal may further be digitized (ADC) for further analysis.

The optimization methods and steps described above may also be performed, or re-performed, after some period of operation of the device/system. For example, routine or regular re-optimization may be part of the stimulation system. The system may then automatically or semi-automatically select a new optimum electrode/electrode pair (e.g., when using a multi-electrode lead) or suggest repositioning of the electrode or lead, if the artifact index falls outside of a present or input range or threshold.

While the systems, devices and methods herein have been described in some detail by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What may be claimed is:

1. A method of optimizing the position of an electrode relative to a subject's inflammatory reflex, the method comprising:
    implanting an electrode in electrical communication with either the vagus nerve, the splenic nerve, the hepatic nerve or the trigeminal nerve so the electrode can be stimulated to inhibit inflammation:
    applying an electrical stimulus to electrode;
    detecting a stimulation artifact;
    determining an indicator of the power of the stimulation artifact, wherein the step of determining an indicator of the power of the stimulation artifact includes calculating the power of the stimulation artifact and a second stimulation artifact; and
    adjusting the position of the stimulation electrode based on the indicator of the power of the stimulation artifact.

2. The method of claim 1, wherein the step of detecting the stimulation artifact comprises detecting the stimulation artifact between the applied stimulation.

3. The method of claim 1, wherein the stimulation artifact is selected from the group consisting of: EMG, EKG, and evoked potentials.

4. The method of claim 1, further comprising detecting a second stimulation artifact.

5. The method of claim 1, further comprising displaying an indicator of the power of the stimulation artifact.

6. The method of claim 1, wherein the step of implanting the electrode comprises implanting a probe having a plurality of electrodes thereon.

7. The method of claim 1, further comprising applying an electrical stimulus to a second electrode and detecting a second stimulation artifact associated with the stimulus from the second electrode; further comprising determining an indicator of the power of the second stimulation artifact.

8. The method of claim 1, further comprising measuring one or more indicators of inflammation.

9. The method of claim 8, further comprising determining a level of inhibition of inflammation based on the measurement of one or more indicators of inflammation.

10. The method of claim 8, further comprising adjusting the position of the stimulation electrode based on the measurement of one or more indicators of inflammation.

11. The method of claim 8, wherein the one or more indicators of inflammation is the level of a biomarker.

12. The method of claim 11, wherein the biomarker is CD11.

13. The method of claim 8, wherein the one or more indicators of inflammation is the level of a neurotransmitter.

14. The method of claim 13, wherein the neurotransmitter is acetylcholine.

15. The method of claim 8, wherein the one or more indicators of inflammation is body temperature.

16. The method of claim 8, wherein the one or more indicators of inflammation is the distribution of cell types.

17. The method of claim 16, wherein the distribution of cell types include granulocyte distribution.

18. A method of optimizing the position of an electrode relative to a subject's inflammatory reflex, the method comprising:
    implanting an electrode in electrical communication with either the vagus nerve, the splenic nerve, the hepatic nerve or the trigeminal nerve so the electrode can be stimulated to inhibit inflammation:
    applying an electrical stimulus to electrode;
    detecting a stimulation artifact;
    determining an indicator of the power of the stimulation artifact;
    adjusting the position of the stimulation electrode based on the indicator of the power of the stimulation artifact; and
    repeating the steps of applying an electrical stimulus to the electrode and detecting the stimulation artifact; further wherein the step of determining the indicator of the power of the stimulation artifact comprises averaging the detected stimulation artifacts to determine the indicator of the power of the stimulation artifact.

* * * * *

UNITED STATES PATENT AND TRADEMARK OFFICE
CERTIFICATE OF CORRECTION

| | |
|---|---|
| PATENT NO. | : 8,412,338 B2 |
| APPLICATION NO. | : 12/620413 |
| DATED | : April 2, 2013 |
| INVENTOR(S) | : Michael A. Faltys |

It is certified that error appears in the above-identified patent and that said Letters Patent is hereby corrected as shown below:

Title Page, Column 1, Lines 1-3; Item (54) and in the Specifications, Column 1, Lines 1-3; delete "DEVICES AND METHODS FOR OPTIMIZING ELECTRODE PLACEMENT FOR ANTI-INFLAMATORY STIMULATION" and insert --DEVICES AND METHODS FOR OPTIMIZING ELECTRODE PLACEMENT FOR ANTI-INFLAMMATORY STIMULATION--.

In the Specifications

Column 4, line 40; after "simulation of a portion", delete "f" and insert --of--.

Signed and Sealed this
Fourth Day of February, 2014

Michelle K. Lee
*Deputy Director of the United States Patent and Trademark Office*